United States Patent [19]

Hirschmann

[11] 3,947,409

[45] Mar. 30, 1976

[54] 16-ALKYL-1,4,9-(11)-PREGNATRIENES AND 9,11-EPOXIDES THEREOF

[75] Inventor: Ralph F. Hirschmann, Scotch Plains, N.J.

[73] Assignee: Merck & Co., Inc., Rahway, N.J.

[22] Filed: Oct. 11, 1974

[21] Appl. No.: 514,161

Related U.S. Application Data

[63] Continuation of Ser. No. 106,591, Jan. 14, 1971, which is a continuation of Ser. No. 669,254, Sept. 20, 1967, abandoned, which is a continuation-in-part of Ser. No. 261,812, Feb. 28, 1963, abandoned, which is a continuation-in-part of Ser. No. 742,993, June, 1958, abandoned.

[52] U.S. Cl.. 260/239.55 R; 260/397.45; 260/239.5
[51] Int. Cl.²............... C07J 7/00; C07J 1/00
[58] Field of Search............... 260/239.55, 397.45

[56] References Cited
UNITED STATES PATENTS 3,164,618  1/1965  Rausser et al. ............... 260/397.45

*Primary Examiner*—Elbert L. Roberts
*Attorney, Agent, or Firm*—Frank M. Mahon; Henry H. Bassford, Jr.; James A. Arno

[57] ABSTRACT

The invention disclosed herein relates to processes and intermediates useful in the preparation of certain 16-lower alkyl-1,4-pregnadiene compounds. It is particularly concerned with novel methods of preparing 16-lower alkyl-9α-fluoro-11β,17α,21-trihydroxy-1,4-pregndiene-3,20-dione and esters thereof, and with novel intermediates useful in these novel methods. It is further concerned with 16-lower alkyl-1,4,9(11)-pregnatriene-17α,21-diol-3,20-diones and their 21-lower alkanoates which, in addition to being valuable as intermediates, are valuable diuretic agents useful in the treatment of edema.

3 Claims, No Drawings

16-ALKYL-1,4,9(11)-PREGNATRIENES AND 9,11-EPOXIDES THEREOF

This is a continuation of application Ser. No. 106,591, filed Jan. 14, 1971, which in turn is a streamlined continuation of 669,254, filed Sept. 20, 1967 (now abandoned), which in turn is a continuation-in-part of 261,812, filed Feb. 28, 1963 (now abandoned), which in turn is a continuation-in-part of 742,993, filed June 19, 1958 (now abandoned).

Since the initial discovery that cortisone was effective in the treatment of rheumatoid arthritis, a number of other related compounds have been prepared having similar anti-inflammatory activity. It has been found that 16 ($\alpha$ and $\beta$)-methyl-9$\alpha$-fluoro-11$\beta$,17$\alpha$,21-trihydroxy-1,4-pregnadiene-3,20-dione possess extremely high anti-inflammatory activity and, in addition, are non-salt retaining. This increased activity permits administration of these compounds in extremely low dosages thereby minimizing undesired side effects.

It is an object of the present invention to provide a new method of preparing these highly active steroids, the 16 ($\alpha$ and $\beta$)-methyl-9$\alpha$-fluoro-11$\beta$,17$\alpha$,21-trihydroxy-1,4-pregnadiene-3,20-diones, as well as other 16-lower alkyl analogues thereof. Another object is to provide novel intermediates useful in the synthesis of said highly active steroids as, for example, 16-lower alkyl-1,4,9(11)-pregnatriene-17$\alpha$,21-diol-3,20-diones and 21-lower alkanoates thereof, which possess useful diuretic activity, and are valuable in the control of edematous conditions. Other objects will be apparent from the detailed description of my invention as hereinafter provided.

In accordance with one embodiment of the present invention, it is now found that 21-acylates of 16$\alpha$-methyl-11$\beta$,17$\alpha$,21-trihydroxy-1,4-pregnadiene-3,20-dione can be converted to the corresponding 9$\alpha$-fluoro compound by procedures which may be depicted structurally as follows:

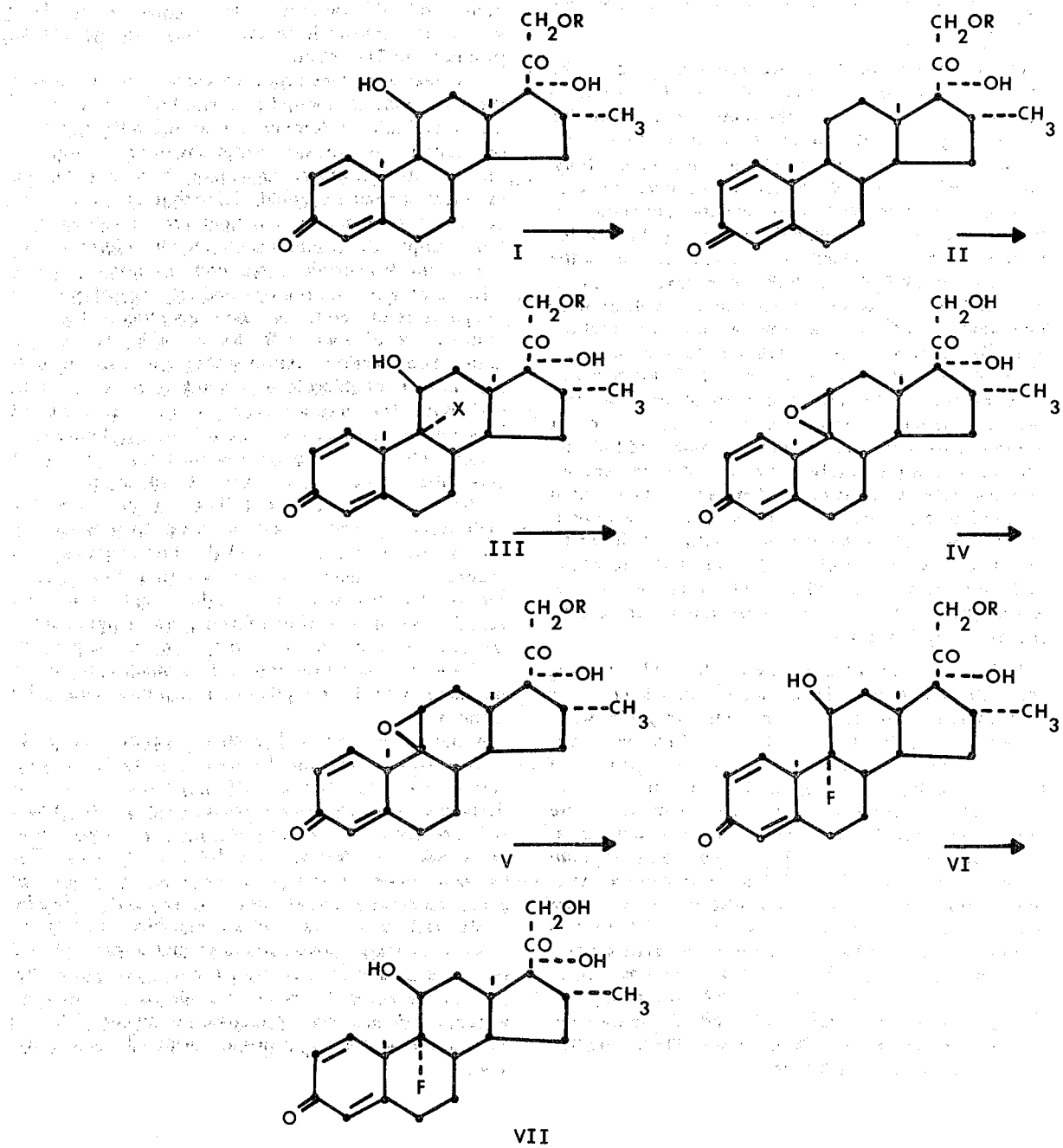

wherein R represents a carboxylic acid radical and X is chlorine or bromine.

In the foregoing process the starting compound, 16α-methyl-11β,17α,21-trihydroxy-1,4-pregnadiene-3,20-dione-21-acylate (I) is first reacted with a dehydrating agent to obtain the corresponding triene, 16α-methyl-17α,21-dihydroxy-1,4,9(11)-pregnatriene-3,20-dione-21 acylate (II). The reaction of this compound with hypochlorous or hypobromus acid produces the corresponding 9α-halo compound, namely, 16α-methyl-9α-halo-11β,17α,21-trihydroxy-1,4-pregnadiene-3,20-dione-21-acylate (III). When this 9α-halo compound is reacted with an alkali the 9,11-oxido compound (IV) is obtained. Since the treatment with alkali also partly cleaves the 21-acylate the reaction product is acylated by reaction with the appropriate acylating agent to produce the 21-acyloxy compound (V). Reaction of the latter compound with hydrogen fluoride affords 16α-methyl-9α-fluoro-11β,17α,21-trihydroxy-1,4-pregnadiene-3,20-dione-21-acylate (VI) which upon hydrolysis is converted to the corresponding free alcohol (VII).

In the first step of the above-described process, the starting compound is reacted with a suitable dehydrating agent to form the correspondng triene. Suitable dehydrating agents for this reaction that might be mentioned are methyl chlorosulfinate, methanesulfonyl chloride and the like. Alternatively, in accordance with a preferred embodiment of this invention, the dehydration is effected by intimately contacting the starting material with N-bromoacetamide and then treating the resulting reaction product with sulfur dioxide. In carrying out the dehydration in accordance with another embodiment of this invention, the 16α-methyl-11β,17α,21-trihydroxy-1,4-pregnadiene-3,20-dione-21-acylate is intimately contacted with the methanesulfonyl chloride in the presence of pyridine. If desired, the reaction can be carried out in a suitable solvent for the reactants such as dimethyl-formamide and the like. The reaction is preferably carried out at a temperature of above 50°C. since at such temperatures the reaction is complete in a short time. For example, the reaction is effected by heating the reaction mixture at 80–85°C. for about 1 hour. After completion of the reaction, methanol and water are added to the reaction mixture, whereupon the desired product precipitates and can be recovered by filtration.

The second step of the process is effected by reacting the triene or anhydro (II) compound with a hypohalous acid wherein the halogen has an atomic weight between 35–80, namely, bromine or chlorine. This reaction is most conveniently effected by reacting a suspension of the triene compound in a suitable watermiscible solvent such as acetone with an aqueous solution of the hypohalous acid. The hypohalous acid solution is conveniently prepared in situ by reacting the appropriate N-halosuccinimide with perchloric acid. For example, the reaction is very conveniently effected by adding an aqueous perchloric acid to a mixture consisting of a suspension of the anhydro compound in acetone and N-bromosuccinimide. After completion of the reaction, any excess of the oxidizing agent is destroyed, for example, by reaction with allyl alcohol, and water is added to the resulting reaction mixture. The halohydrin is then recovered by filtration.

In the following step of my process the halohydrin (III) is reacted with alkaline reagents to form the correspondng 9,11-oxide compound. Although various alkalis can be used for carrying out this reaction, I prefer to use an alkali metal alcoholate, for example, sodium methylate which is inexpensive and readily available. Thus, the reaction is readily effected by dissolving the halohydrin in a suitable solvent such as tetrahydrofuran and methanol and adding a solution of sodium methoxide to the resulting solution. The reaction is complete after a few minutes at room temperature after which any excess base is neutralized and the solvents are removed by evaporation under reduced pressure. The crystalline residue containing the 9,11-oxido compound (IV) can then be purified by crystallization from suitable solvents or solvent mixtures. The reaction with the alkali also results in partial methanolysis of the 21-acyloxy substituent and it is desirable to reacylate the product with a suitable acylating agent to produce the corresponding 21-acylate (V). For example, this is conveniently accomplished by reaction of 9,11-oxido compound (IV) obtained after treatment with alkali with acetic anhydride in the presence of pyridine to produce the 21-acetate.

The next step of my process is carried out by reacting the 9,11-oxide compound (V) with hydrogen fluoride. This reaction is preferably carried out in the presence of a suitable solvent, such as tetrahydrofuran or a mixture of tetrahydrofuran and chloroform. For the obtainment of maximum yields, I find that it is desirable to carry out the reaction at temperatures of about 0°C. For example, the reaction is effected by adding a solution of the 9,11-oxido compound in chloroform to a mixture of hydrogen fluoride and tetrahydrofuran at a temperature of –60°C. and then aging the mixture at a temperature of about 0°C. for an additional 4 to 5 hours. The reaction mixture is then quenched by adding a mixture of chloroform, ice and aqueous potassium carbonate. The chloroform layer is then separated and concentrated down to a small volume and benzene is added, whereupon the desired 9α-fluoro compound crystallizes and can be recovered by filtration.

The 9α-fluoro-21-acetate (VI) so obtained is readily hydrolyzed by reaction with an alkali to produce the correspondng free alcohol (VII). For example, this reaction is effected by treating a solution of the ester in methanol with a solution of sodium methoxide. The reaction is complete after a few minutes. After neutralizing the reaction mixture, adding water to the neutralized solution, and evaporating to a small volume the free alcohol (VII) precipitates and can be separated by filtration.

In the above-described reaction procedures, the 21-hydroxy-substituent can be protected by being converted to a suitable acylate. Although various acylated derivatives are useful in the processes of this invention, it is preferred to use the derivatives of hydrocarbon carboxylic acids having from 1–9 carbon atoms. For example, esters of acids such as acetic acid, propionic acid, butyric acid, and the like, esters of aryl carboxylic acids, such as benzoic acid and the like, or esters of aralkyl carboxylic acids such as phenyl acetic acid, and the like are suitable in carrying out the processes of the present invention. These acylated derivatives are conveniently prepared from the corresponding free alcohol by reaction with the appropriate carboxylic acid anhydride.

The following examples are presented to illustrate the processes for carrying out the present invention.

EXAMPLE 1

16α-Methyl-17α,21-Dihydroxy-1,4,9(11)-Pregnatriene-3,20-Dione-21-Acetate

About 11.7 g. of 16α-methyl-11β,17α,21-trihydroxy-1,4-pregnadiene-3,20-dione-21-acetate is dissolved in a mixture of 65 ml. of dimethylformamide and 11 cc. of pyridine in a dry 2 liter, 3 necked flask fitted with a stirrer. To the resulting solution is added 5.55 ml. of methanesulfonyl chloride and the reaction mixture maintained at 80°–85°C. for about 1 hour. The resulting red solution is cooled in an ice bath and treated successively with 110 ml. of methanol, 480 cc. of 5% aqueous sodium bicarbonate and finally with 360 ml. of water. The resulting reaction mixture is then allowed to stand at room temperature overnight after which the precipitated product is removed by filtration, washed repeatedly with water and dried to a constant weight in air at about 50°C. The 16α-methyl-17α,21-dihydroxy-1,4,9(11)-pregnatriene-3,20-dione-21-acetate so obtained melts at 206°–211°C. with previous softening, giving a red melt. On paper stripping, this product is a single spot material in the methanol-formamide (2:1) benzene system. (rf=0.74).

Hydrolysis of the acetate ester with a base, for example, sodium methoxide in methanol, affords the free alcohol, 16α-methyl-17α,21-dihydroxy-1,4,9(11)-pregnatriene-3,20-dione.

The starting material employed in the foregoing process is prepared as follows:

A mixture of 15.51 grams of 16α-methyl-11β,17α,21-trihydroxy-1,4-pregnadiene-3,20-dione in 43 mls. of pyridine and 10 ml. of acetic anhydride is heated at 52°C. for 1¼ hours in a nitrogen atmosphere. The steroid dissolves immediately on heating. The mixture is cooled to 40°C. and 280 ml. of water is added with constant stirrng over a 30 minute interval while keeping the temperature at 40°C. The reaction mixture is then aged at 0°C. for about 1 hour and the precipitated product removed by filtration, washed free of pyridine and acetic acid with water and dried at about 47°–48°C. in air to constant weight. The 16α-methyl-11β,17α,21-trihydroxy-1,4-pregnadiene-3,20-dione-21-acetate melts at 140°–147°C. and is a single spot material, rf=0.86, in the methanol-formamide (2:1) chloroform system.

EXAMPLE 2

16α-Methyl-9α-Bromo-11β,17α,21-Trihydroxy-1,4-Pregnadiene-3,20-Dione-21-Acetate

To a suspension of 9.03 grams of 16α-methyl-17α,21-dihydroxy-1,4,9(11)-pregnatriene-3,20-dione-21-acetate in 114 ml. of acetone is added at 0°C. with stirring 5.93 grams of N-bromosuccinimide and then 20.4 ml. of a perchloric acid solution prepared by dissolving 0.548 ml. of 70% perchloric acid in 33 ml. of water. The resulting reaction mixture is stirred at 0°C. for about 4¾ hours. The excess of N-bromosuccinimide is destroyed by the addition of about 40 drops of allyl alcohol and 500 ml. of water is then added with stirring. This mixture is held at 0°C. for about 1 hour. The precipitated 16α-methyl-9α-bromo-11β,17α,21-trihydroxy-1,4-pregnadiene-3,20-dione-21 acetate is recovered by filtration, washed repeatedly with water and dried in a desiccator over sulfuric acid at 0.1 mm. overnight.

A solution of 250 mg. of the bromohydrin in 5 ml. of 0.25 N perchloric acid in methanol is stirred for about 18 hours at room temperature to produce 16α-methyl-9α-bromo-11β,17α,21-trihydroxy-1,4-pregnadiene-3,20-dione which is recovered by adding water to the reaction mixture and allowing the product to crystallize.

EXAMPLE 3

16α-Methyl-9α-Chloro-11β,17α,21-Trihydroxy-1,4-Pregnadiene-3,20-Dione-21-Acetate When the process of Example 2 is repeated using N-chlorosuccinimide in place of N-bromosuccinimide, 16α-methyl-9α-chloro-11β,17α,21-trihydroxy-1,4-pregnadiene-3,20-dione-21-acetate is obtained.

EXAMPLE 4

16α-Methyl-9,11-Oxido-17α,21-Dihydroxy-1,4-Pregnadiene-3,20-Dione and
16α-Methyl-9,11-Oxido-17α,21-Dihydroxy-1,4-Pregnadiene-3,20-dione-21-acetate 10.48 Grams of 16α-methyl-9α-bromo-11β,17α,21-trihydroxy-1,4-pregnadiene-3,20-dione 21-acetate is dissolved in a 76.5 ml. of tetrahydrofuran and 38 ml. of methanol. This mixture is treated with 25.8 ml. of 0.91 N sodium methoxide in methanol in a nitrogen atmosphere at about 24°C. for 5 minutes. The excess base is neutralized by the addition of an excess (1.58 ml.) of glacial acetic acid which results in a color change from red to dark yellow. The solution is evaporated in vacuo at 45°–48°C. bath temperature. The resulting crystalline residue is flushed with chloroform and then with petroleum ether. The pale brown residue, a mixture of 16α-methyl-9,11-oxido-17α,21-dihydroxy-1,4-pregnadiene-3,20-dione and the 21-acetate derivative is suspended in 48 ml. of pyridine and 24 ml. of acetic anhydride and heated under nitrogen at about 65°C. for 1⅓ hours. After removal of the solvents in vacuo, in a water bath up to 70°C., the solid residue is flushed with petroleum ether. About 80 ml. of water is added and the resulting acetate ester is filtered off and washed thoroughly with water. The crude produce is dissolved in 88 ml. of acetone giving a turbid, reddish-brown solution which is treated with 1 g. of activated charcoal and filtered. The activated charcoal is removed by filtration and washed free of steroid with acetone. The clear, reddish brown filtrate is concentrated to a volume of about 8 ml. on a steam bath in a current of nitrogen and 80 ml. of petroleum ether addd. The precipitate, 16α-methyl-9,11-oxido-17α,21-dihydroxy-1,4-pregnadiene-3,20-dione-21-acetate, is filtered, washed with acetone: petroleum ether (1:10) to yield a yellow to pale brown solid melting at 181°–187°C. (inserted at 165°C.).

Hydrolysis of the acetate ester with a base, for example, sodium methoxide in methanol affords the free alcohol, 16α-methyl-9,11-oxido-17α,21-dihydroxy-1,4-pregnadiene-3,20-dione.

EXAMPLE 5

16α-Methyl-9,11-Oxido-17α,21-Dihydroxy-1,4-Pregnadiene-3,20-Dione-21-acetate

When the process of Example 4 is repeated using 16α-methyl-1,4-pregnadiene-9α-chloro-11β,17α,21- triol-3,20-dione-21-acetate as the starting material 16α-methyl-9,11-oxido-17α,21-dihydroxy-1,4-pregnadiene-3,20-dione-21-acetate is obtained.

EXAMPLE 6

16α-Methyl-9α-Fluoro-11β,17α,21-Trihydroxy-1,4-Pregnadiene-3,20-Dione-21-Acetate A mixture of 18.9 ml. of a hydrogen fluoride in tetrahydrofuran mixture (2:1 by weight), 9.7 ml. of chloroform and 12.5 ml. of tetrahydrofuran is chilled in an acetone-Dry Ice bath, and a solution of 7.62 grams of 16α-methyl-9,11-oxido-17α,21-dihydroxy-1,4-pregnadiene-3,20-dione-21-acetate in 67 ml. of chloroform (cooled to −60°C.) is added. The mixture is held at 0°C. for about 4¼ hours, again chilled to −60°C. and quenched into a mixture of 105 ml. of chloroform, 50 grams of ice and about 55 grams of potassium carbonate in 45 ml. of water. Solid potassium carbonate is added to keep the final pH at about 7–8. The layers are separated and the aqueous phase is backextracted twice with chloroform. The combined organic layers are washed twice with water and once with a saturated solution of sodium chloride. After drying over magnesium sulfate, the solution is concentrated to a volume of about 25 ml. After some crystallization of product has occurred, about 63 ml. of benzene is added. The product is allowed to crystallize overnight. The product, 16α-methyl-9α-fluoro-11β,17α,21-trihydroxy-1,4-pregnadiene-3,20-dione-21 acetate, is isolated by filtration and washed with benzene. The product has $\lambda_{max}$.CH$_3$OH 238 mµ (E% 319).

EXAMPLE 7

16α-Methyl-9α-Fluoro-11β,17α,21-Trihydroxy-1,4-Pregnadiene-3,20-Dione

A 5.270 g. aliquot of the product obtained in Example 6 is dissolved in 200 ml. of methanol. The resulting solution is treated with 12.3 ml. of 0.91 N sodium methoxide in a nitrogen atmosphere. The mixture is stirred at 24°C. for 7 minutes and 1.76 ml. of glacial acetic acid is added. The resulting solution is treated with about 400 mg. of activated carbon which is removed by filtration after stirring for about 10 minutes. After washing the activated carbon free of steroid, the filtrate is diluted with 200 ml. of water and then concentrated to a volume of about 140 ml. The product 16α-methyl-9α-fluoro-11β,17α,21-triol-1,4-pregnadiene-3,20-dione is recovered by filtration, washed with water and dried. The product so obtained melts at about 263°C. (dec.) when inserted at 245°, $\lambda_{max}$.CH$_3$OH238 mµ (E% 390); $\lambda_{max}$H$_2$SO$_4$−15 min. (after removal of CH$_3$OH) 308mµ (341), 258 mµ (492); $\lambda_{max}$H$_2$SO$_4$−2 hrs. (after removal of CH$_3$OH) 306 mµ (375), 258 mµ (592).

An aliquot is dried at 100° for 1 hour (0.1 mm) and shows $\lambda_{max}$CH$_3$OH 238 mµ (E% 397); $\lambda_{max}$H$_2$SO$_4$−2 hrs. (after removal of CH$_3$OH) 397 mµ (351), 262 mµ (446); $\lambda_{max}$H$_2$SO$_4$−2 hrs. (on solid) 307 mµ (360), 262 mµ (442). Anal. Calc'd. for $C_{22}H_{29}O_5F$: C, 67.33; H, 7.45. Found: C, 67.53; H, 7.22.

EXAMPLE 8

To a solution of 6.78 g. of 16α-methylprednisolone acetate (16.3 millimoles) in 10 ml. of pyridine is added 24.8 millimols of N-bromoacetamie. The mixture is stirred at 10° C. for 15 minutes in a nitrogen atmosphere. The mixture is cooled to 0°–2°C. with an acetone-Dry Ice bath and anhydrous sulfur dioxide is passed over the reaction mixture for about 1–2 minutes at such a rate that the temperature — with external cooling — does not rise above 15°C. The reaction mixture — a thick slurry which gives a negative starch potassium iodide test — is allowed to come to 12°C. At this temperature much of the solid redissolves and the mixture is added slowly with stirring over a 15-minute interval to ice-water. The mixture is aged at 5°C. for ½ hour, filtered and the product is washed with water. The olefin is dried at 50°C. overnight. The product, which still contains pyridine, weighs 8.71 g., $\lambda_{max}$.MeOH 240 mµ (E% 272). Paper strip in benzene shows the olefin to be single spot material except for the origin impurity (neg. TZ test, $\lambda_{max}$ 6.35 µ, also present in the starting material). The olefin is dissolved in chloroform, and washed three times with 2.5 N hydrochloric acid and with water. The combined water washes are back-extracted with chloroform and the combined organic layers are filtered and taken to dryness. The residue is flushed with petroleum ether and dried to constant weight to obtain 5.91 g. of 16α-methyl-17α,21-dihydroxy-1,4,9(11)-pregnatriene-3,20-dione-21-acetate, $\lambda_{max}$MeOH 240 mµ (E% 370).

EXAMPLE 9

In accordance with the procedure described in Example 1, 16α-ethyl-11β,17α,21-trihydroxy-1,4-pregnadiene-3,20-dione 21-acetate is treated with methanesulfonyl chloride in dimethylformamide and pyridine to produce 16α-ethyl-17α,21-dihydroxy-1,4,9(11)-pregnatriene-3,20-dione-21-acetate which, upon hydrolysis with sodium methoxide in methanol, forms 16α-ethyl-17α,21-dihydroxy-1,4,9(11)-pregnatriene-3,20-dione. Similarly, starting with 16α-butyl-11β,17α,21-trihydroxy-1,4-pregnadiene-3,20-dione-21-acetate, there are obtained 16α-butyl-17α,21-dihydroxy-1,4,9(11)-pregnatriene-3,20-dione and its 21-acetate.

EXAMPLE 10

16β-Methyl-17α,21-Dihydroxy-1,4,9(11)-Pregnatriene-3,20-Dione and its 21-Acetate About 11.7 g. of 16β-methyl-11β,17α,21-trihydroxy-1,4-pregnadiene-3,20-dione 21-acetate is dissolved in a mixture of 65 ml. of dimethylformamide and 11 cc. of pyridine in a dry 2 liter, 3 necked flask fitted with a stirrer. To the resultng solution is added 5.55 ml. of methanesulfonyl chloride and the reaction mixture maintained at 80°–85°C. for about 1 hour. The resulting red solution is cooled in an ice bath and treated successively with 110 ml. of methanol, 480 cc. of 5% aqueous sodium bicarbonate and finally with 360 ml. of water. The resulting reaction mixture is then allowed to stand at room temperature over night after which the precipitated product is removed by filtration, washed repeatedly with water and dried to a constant weight in air at about 50°C. to give 16β-methyl-17α,21-dihydroxy-1,4,9(11)-pregnatriene-3,20-dione 21-acetate. Hydrolysis of the acetate ester with a base, for example, sodium methoxide in methanol, affords the free alcohol, 16β-methyl-17α,21-dihydroxy-1,4,9(11)-pregnatriene-3,20-dione.

EXAMPLE 11

In accordance with the procedure described in Example 1, 16β-ethyl-11β,17α,21-trihydroxy-1,4-pregnadiene-3,20-dione 21-acetate is treated with methanesulfonyl chloride in dimethylformamide and pyridine to produce 16β-ethyl-17α,21-dihydroxy-1,4,9(11)-pregnatriene-3,20-dione 21-acetate which, upon hydrolysis with sodium methoxide in methanol, forms 16β-ethyl-17α,21-dihydroxy-1,4,9(11)-pregnatriene-3,20-dione. Similarly, starting with 16β-butyl-11β,17α,21-trihydroxy-1,4-pregnadiene-3,20-dione 21-acetate, there is obtained 16β-butyl-17α,21-dihydroxy-1,4,9(11)-pregnatriene-3,20-dione and its 21-acetate. Similarly, starting with 16β-isopropyl-11β,17α,21-trihydroxy-1,4-pregnadiene-3,20-dione 21-acetate and 16β-amyl-11β,17α,21-trihydroxy-1,4-pregnadiene-3,20-dione 21-acetate, there are obtained respectively, 16β-isopropyl-17α,21-dihydroxy-1,4,9(11)-pregnatriene-3,20-dione and 16β-amyl-17α,21-hydroxy-1,4,9(11)-pregnatriene-3,20-dione, and their 21-acetates.

The 16α-methyl-11β,17α,21-trihydroxy-1,4-pregnadiene-3,20-dione-21-acetate used as the starting material in Example 1 can be prepared as follows:

3α-Acetoxy-16-pregnene-11,20-dione is reacted with methyl magnesium iodide in the presence of cuprous chloride thereby forming 16α-methyl-3α-hydroxypregnane-11,20-dione 3-acetate, which is reacted with aqueous methanolic hydrochloric acid to form 16α-methyl-3α-hydroxy-pregnane-11,20-dione. The latter compound, which is a potent anesthetic, is reacted with acetic anhydride in the presence of p-toluene sulfonic acid catalyst to form a mixture of enol acetate containing 16α-methyl-3α,20-dihydroxy-17,20-pregnene-11-one, 3,20-diacetate; this mixture, after chromatographic purification over acid washed alumina to remove any unchanged starting material, is reacted with perbenzoic acid and the resulting 16α-methyl-17α,20-epoxy-3α,20-dihydroxy-pregnane-11-one 3,20-diacetate is hydrolyzed with methanolic potassium bicarbonate to produce 16α-methyl-3α,17α-dihydroxy-pregnane-11,20-dione. The latter compound is reacted with bromine in chloroform to form 21-bromo-16α-methyl-3α,17α-dihydroxy-pregnane-11,20-dione which is reacted with sodium iodide in acetone to produce 21-iodo-16α-methyl-3α,17α-dihydroxy-pregnane-11,20-dione which is converted without isolation to 16α-methyl-3α,17α,21-trihydroxy-pregnane-11,20-dione-21-acetate by reaction with anhydrous potassium acetate; this compound is reacted with chromium trioxide in pyridine to form 16α-methyl-17α,21-dihydroxy pregnane-3,11,20-trione 21-acetate. The 16α-methyl-16α,21-dihydroxy-pregnane-3,11,20-trione 21-acetate is reacted with bromine in glacial acetic acid-chloroform to produce 4-bromo-16α-methyl-17α,21-dihydroxy-pregnane-3,11,20-trione, which is then reacted with semicarbazide to form 16α-methyl-17α,21-dihydroxy-4-pregnene-3,11,20-trione 3,20-bissemicarbazone 21-acetate. This 3,20-bissemicarbazone is reacted with sodium borohydride to form 16α-methyl-11β,17α,21-trihydroxy-4-pregnene-3,20-dione 3,20-bissemicarbazone which is hydrolyzed under acid conditions to form 16α-methyl-11β,17α,21-trihydroxy-4-pregnene-3,20-dione. This latter compound is then converted to the corresponding 1,4-pregnadiene compound by contacting it with the dehydrogenating activity of microorganisms of the Class Schizomycetes, for example, *Bacillus sphaericus* (ATCC-245) or *Nocardia asteroides* (ATCC 9970). The 16α-methyl-11β,17α,21-trihydroxy-1,4-pregnadiene-3,20-dione so obtained is then reacted with acetic anhydride in the presence of pyridine to produce the corresponding 16α-methyl-11β,17α,21-trihydroxy-1,4-pregnadiene-3,20-dione-21-acetate.

Similarly, but using other lower alkyl magnesium iodides such as ethyl magnesium iodide, butyl magnesium iodide, and the like, in the above-described reaction with 3α-acetoxy-16-pregnene-11,20-dione, there is obtained the correspondng 16α-lower alkyl-3α-acetoxy-pregnane-11,20-dione which, upon treatment in accordance with reaction sequence employed hereinabove, is converted to the corresponding 16α-lower alkyl-11β,17α,21-trihydroxy-1,4-pregnadiene-3,20-dione 21-acetate, such as 16α-ethyl-11β,17α,21-trihydroxy-1,4-pregnadiene-3,20-dione 21-acetate, 16α-propyl-11β,17α,21-trihydroxy-1,4-pregnadiene-3,20-dione 21-acetate, and the like.

In the same way, other 21-acylates, in particular those in which the acyl substituent is a radical of a hydrocarbon carboxylic acid having from one to nine carbon atoms, which are especially suitable starting materials for the processes of the present invention, are obtained. Thus, upon intimately contacting the 16α-methyl-(or other 16α-lower alkyl)-11β,17α,21-trihydroxy-1,4-pregnadiene-3,20-dione with benzoic acid anhydride, butyric acid anhydride, phenylacetic acid anhydride, succinic acid anhydride, and the like, the corresponding 21-acylate is obtained.

Instead of using 16α-lower alkyl-11β,17α,21-trihydroxy-1,4-pregnadiene-3,20-dione 21-acetate as starting material, the 16β-lower alkyl epimer may be employed. For example, the 16β-methyl-11β,17α,21-trihydroxy-1,4-pregnadiene-3,20-dione 21-acetate starting material may be prepared as follows:

Diazomethane is generated by warming the generation flask to 40°–45°C. and cautiously adding the N-methyl-N-nitrosotosylamide-ether from the dropping funnel. Nitrogen is utilized to sweep the diazomethane into a solution of 20 g. of 3α-acetoxy-16-pregnene-11,20-dione in 100 ml. of tetrahydrofuran and 120 ml. of ether. The process is continued until the steroid solution remains yellow for several hours. The product, 3α-acetoxy-16α,17α-methyleneazopregnane-11,20-dione largely precipitates from the reaction mixture. After 16 hours, the mixture is filtered, washed with ether and dried in air. Yield about 14 grams.

37.4 g. of 3α-acetoxy-16α,17α-methyleneazopregnane-11,20-dione is placed in a 500 ml. round-bottom flask and heated by an oil bath in vacuo (pressure 0.6 mm.). A manometer and 12-liter surge flask are in the line between the reaction flask and pump trap. When the bath temperature reaches 180°C. the 3α-acetoxy-16α,17α-methyleneazo-pregnane-11,20-dione begins to melt with evolution of nitrogen. The maximum pressure reached is 83 mm. After 10 minutes at 180°–182°C. the melt is cooled. It has $\lambda_{max}CH_3OH$ 249 E percent 191, and is taken up in about 150 ml. of acetone, filtered through diatomaceous earth, concentrated to about 110 ml., and ether is slowly added to the boiling solution until crystallization occurs. These crystals of 3α-acetoxy-16-methyl-16-pregnene-11,20-dione weigh about 19.0 g.

A solution of 20.0 g. of 3α-acetoxy-16-methyl-16-pregnene-11,20-dione dissolved in 600 ml. of methanol, is cooled to 18°C., and 80 ml. of 30% hydrogen peroxide followed by 80 ml. of 2.5 N sodiim hydroxide are added. Considerable material precipitates from solution, but all redissolves on stirring the reaction mixture at 25°–30°C. for 40 minutes. The solution is kept at 15°–20°C. for 18 hours at which time the ultraviolet maximum at 249 has completely disappeared. Then 600 ml. of saturated salt water is slowly added, the crystalline precipitate is filtered, washed with water, and dried in air and in vacuum. The 16α,17α-epoxy-3α-hydroxy-16β-methyl-pregnane-11,20-dione thus formed weighs about 17 g.

To a solution of 2.69 g. of 16α,17α-epoxy-3α-hydroxy-16β-methyl-pregnane-11,20-dione in 55 ml. dioxane is added 27 ml. of 2 M aqueous perchloric acid. The clear solution is kept at 25°–30°C. for 65 hours. Cold water (175 ml.) is added, the slurry chilled to 8°C. and filtered after 30 minutes. The precipitate, containing a mixture of 3α,17α-dihydroxy-16-methyl-15-pregnene-11,20-dione and 3α,17α-dihydroxy-16methylene-pregnane-11,20-dione is washed with water, and dried in air and finally at 50°C. in vacuum. Yield: approximately 2 g.; the relative proportion of 3α,17α-dihydroxy-16-methyl-15-pregnene-11,20-dione and 3α,17α-hydroxy-16-methylene-pregnane-11,20-dione is estimated to be of the order of 1:1.

A solution 3.05 g. (8.47 millimols) of the olefin mixture of 3α,17α-dihydroxy-16-methyl-15-pregnene-11,20-dione and 3α,17α-dihydroxy-16-methylene-pregnane-11,20-dione in 80 ml. of methanol is reduced in hydrogen at 1 atmosphere and 25°C. in the presence of 2.0 g. of 25% palladium-calcium carbonate catalyst. Modification of the hydrogen conditions, pH, solvent, catalyst, etc. alters the isomer ratio significantly. Uptake of the calculated amount of hydrogen is complete in 45 minutes. The mixture is stirred an additional 30 minutes and filtered through diatomaceous earth. The colorless filtrate is taken to dryness and crystallized from ether; a mixture of 3α,17α-dihydroxy-16α-methyl-pregnane-11,20-dione and 3α,17α-dihydroxy-16α-methyl-pregnane-11,20-dione is obtained; weight about 3 g. The product consists of 3α,17α-dihydroxy-16α-methyl-pregnane-11,20-dione and 3α,17α-dihydroxy-16β-methyl-pregnane-11,20-dione in the ratio ca. 7:3 as determined by the amounts of end product isolated below.

One gram of this hydrogenation product containing 3α,17α-dihydroxy-16α-methyl-pregnane-11,20-dione and 3α,17α-dihydroxy 16β-methyl-pregnane-11,20-dione, is chromatographed on 100 g. of activated magnesium silicate. The 100% chloroform eluates give 3α,17α-dihydroxy-16α-methyl-pregnane-11,20-dione, M.P. 188°–191°C: the 5% methanol-chloroform eluates give 3α,17α-dihydroxy-16β-methyl-pregnane-11,20-dione, hexagonal plates from benzene-ethyl-acetate; M.P. 192°–197°C.

A solution of 3.50 g. (9.7 millimols) of 3α,17α-dihydroxy-16β-methyl-pregnane-11,20-dione in 40 mg. of chloroform is warmed to 40°–45°C. A solution of 1.76 g. (11 millimols) of bromine in 25 ml. of chloroform is added dropwise to the stirred solution such that the color is not darker than pale yellow (ca. 2 drops/sec., total time—1 hour). The nearly colorless solution is cooled to 20°C. and 200 ml. of ether is added. The mixture is extracted with excess cold 5% potassium bicarbonate solution, sodium bisulfite solution, and water, and dried over magnesium sulfate. The colorless residue after removal of solvent, 21-bromo-3α,17α-dihydroxy-16β-methyl-pregnane-11,20-dione (about 4 grams) gives a positive tetrazolium test.

To 4.30 g. of 21-bromo-3α,17α-dihydroxy-16β-methyl-pregnane-11,20-dione in 90 ml. of acetone and 0.01 ml. of acetic acid is added 4.83 g. of anhydrous potassium acetate and 3.85 g. of potassium iodide. The stirred mixture is refluxed for 18 hours and concentrated on the water pump to a small volume. Water is added, the product extracted into ethyl acetate, and the organic extract dried over magnesium sulfate to give about 4 grams of a colorless foam that partly crystallizes from acetone-ether to give 3α,17α,21-trihydroxy-16β-methyl-pregnane-11,20-dione 21-acetate.

To a solution of 3α,17α,21-trihydroxy-16β-methyl-pregnane-11,20-dione 21-acetate (4.9 g.) in 100 ml. t-butanol and 20 ml. of water cooled to 10°–15°C., is added 3.5 g. N-bromo-succinimide. The suspension is stirred at 15°C. until all the N-bromosuccinimide has dissolved (90 minutes). The reaction mixture is kept at 2°C. for about sixteen hours and at 25°C. for 2 hours. Sodium sulfite solution is added to destroy bromine and the mixture concentrated on the water pump to a low volume. A granular precipitate forms; water is added, the precipitate filtered and washed with water; chromatography on neutral alumina and elution with mixtures of chloroform and benzene gives 17α,21-dihydroxy-16β-methyl-pregnane-3,11,20-trione 21acetate.

To a stirred solution of 585 mg. of 17α,21-dihydroxy-16β-methyl-pregnane-3,11,20-trione 21-acetate in 10 ml. of acetic acid and 8 ml. of chloroform kept at −10°C. is added slowly 230 mg. of bromine in 6 ml. of chloroform. After addition is complete, 1.2 g. of sodium acetate in 7 ml. of cold water is added and the mixture is extracted with chloroform. The chloroform extract is washed with dilute potassium bicarbonate, water and dried over sodium sulfate. The residue is triturated with ether to give 480 mg. of crystalline 4-bromo-17α,21-dihydroxy-16β-methyl-pregnane-3,11,20-trione 21-acetate.

To 583 mg. of 4-bromo-17α,21-dihydroxy-16β-methyl-pregnane-3,11,20-trione 21-acetate in 20 ml. of acetonitrile under nitrogen is added a slurry of 600 mg. of semicarbizide hydrochloride and 410 mg. sodium bicarbonate in 4 ml. of water. After 2 hours, the acetonitrile is removed in vacuo, water is added and about 540 mg. of crystalline 3-semicarbazone of 17α,21-dihydroxy-16β-methyl-4-pregnene-3,11,20-triene 21acetate filtered, washed with water and dried.

540 mg. of the 3-semicarbazone of 17α,21-dihydroxy-16β-methyl-4-pregnene-3,11,20-trione 21-acetate is dissolved in 20 mg. of acetic acid, 1.5 ml. of pyruvic acid and 5 ml. of water. After 18 hours at 25°C., water is added and the mixture extracted with chloroform. The chloroform extract is washed with aqueous potassium bicarbonate, water and dried over sodium sulfate. Removal of solvent gives crude 17α,21-dihydroxy-16β-methyl-4-pregnene-3,11,20-trione 21-acetate which is purified by chromatography on neutral alumina and crystallization from acetone-ether (hexagonal plates).

To a stirred solution of 500 mg. of 17α,21-dihydroxy-16β-methyl-4-pregnene-3,11,20-trione 21-acetate in 12.5 ml. of methanol and 3 ml. of dimethylformamide kept under nitrogen is added a slurry of 680 mg. of semicarbazide hydrochloride and 370 mg. of sodium bicarbonate in 1 ml. of water. The stirred mixture is refluxed 3½ hours and maintained at 45°C. for 17 hours. It is then cooled to 20°C. and 50 ml. of 50% saturated aqueous sodium chloride is added. After 2 hours at 0°C. the precipitate of 3,20-bis-semicarbazido-17α,21-dihydroxy-16β-methyl-4-pregnene-3,11,20-trione 21-acetate is filtered, washed with water until free of chloride ion and dried in air.

To a stirred solution of 600 mg. of 3,20-bis-semicarbazido-17α,21-dihydroxy-16β-methyl-4-pregnene-3,11,20-trione 21-acetate in 30 ml. of tetrahydrofuran and 11 ml. of water under nitrogen is added 200 mg. powdered sodium borohydride. The stirred suspension is refluxed 45 minutes and then cooled to 15°C. Aqueous acetate acid (3 ml. of 30%) is added cautiously and most of the tetrahydrofuran is removed in vacuum. Addition of 5 ml. of methanol and 5 ml. of water induces the product to crystallize. Following addition of 10 ml. of a saturated sodium chloride solution and aging at 0°C. the product 3,20-bis-semicarbazido-11β,17α,21-trihydroxy-16β-methyl-4-pregnene-3,20-dione is filtered, washed with water, and dried in air.

To a solution of 510 mg. of reduced 3,20-bis-semicarbazido-11β,17α,21-trihydroxy-16β-methyl-4-pregnene-3,20-dione in 5 ml. of acetic acid is added 1.20 ml. of water and 0.50 ml. of pyruvic acid. The solution is kept at 25°C. for 18 hours. Water (20 ml.) is added, and the mixture is extracted thoroughly with chloroform. The chloroform extract is dried over magnesium sulfate and taken to dryness. The residue is crystallized from acetone-ether to give pure 11β,17α,21-trihydroxy-16β-methyl-4-pregnene-3,20-dione.

A solution of 100 mg. of 11β,17α,21-trihydroxy-16β-methyl-4-pregnene-3,20-dione in 1.0 ml. of pyridine and 0.5 ml. of acetic anhydride is prepared. After 18 hours at 25°C., the solution is taken to dryness in vacuo and the solid residue purified by crystallization from acetone-ether to give 11β,17α,21-trihydroxy-16β-methyl-4-pregnene-3,20-dione 21-acetate.

To 100 mg. 11β,17α,21-trihydroxy-16β-methyl-4-pregnene-3,20-dione 21-acetate in 5 ml. of acetic acid is added 50 mg. of selenium dioxide. The mixture is refluxed under nitrogen 18 hours, 50 mg. of selenium dioxide is added and the mixture refluxed in additional 24 hours. The mixture is filtered, and the filtrate taken to dryness. The residue is taken up in ethyl acetate and washed successively with aqueous sodium bicarbonate, ammonium sulfide, dilute ammonia water, water, dilute hydrochloric acid and water and dried over magnesium sulfate. It is then treated with activated charcoal and concentrated to dryness. Crystallization of the residue from acetone-ether gives pure 11β,17α,21-trihydroxy-16β-methyl-1,4-pregnadiene-3,20-dione 21-acetate.

Similarly, but using other diazo-lower alkanes such as diazoethane, diazopropane, and the like, in the above-described reaction with 3α-acetoxy-16-pregnene-11,20-dione, there is obtained the corresponding 3α-acetoxy-16α,17α-alkyleneazo-pregnene-11,20-dione which, upon treatment in accordance with reaction sequence employed hereinabove, is converted to the corresponding 16β-lower alkyl-11β,17α,21-trihydroxy-1,4-pregnadiene-3,20-dione 21-acetate, such as 16β-ethyl-11β,17α,21-trihydroxy-1,4-pregnadiene-3,20-dione 21-acetate, 16β-propyl-11β,17α,21-trihydroxy-1,4-pregnadiene-3,20-dione 21-acetate, and the like.

In the same way, other 21-acylates, in particular those in which the acyl substituent is a radical of a hydrocarbon carboxylic acid having from one to nine carbon atoms, which are especially suitable starting materials for the processes of the present invention, are obtained. Thus, upon intimately contacting the 16β-methyl(or other 16β-lower alkyl)-11β,17α,21-trihydroxy-1,4-pregnadiene-3,20-dione with benzoic acid anhydride, butyric acid anhydride, phenylacetic acid anhydride, succinic acid anhydride, and the like, the corresponding 21-acylate is obtained.

Various changes and modifications may be made in carrying out the present invention without departing from the spirit and scope thereof. Insofar as these changes and modifications are within the puriview of the annexed claims, they are to be considered as part of my invention.

What is claimed is:

1. A 16α-methyl-1,4-pregnadiene compound of the formula:

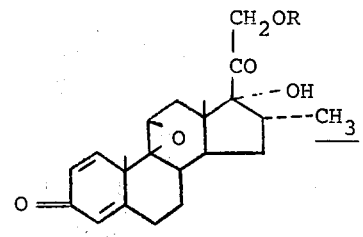

wherein R is from the group consisting of hydrogen and a hydrocarbon carboxylic acid radical having from one to nine carbon atoms.

2. A compound as defined in claim 1 having the chemical name 16α-methyl-9,11-oxido-17α,21-dihydroxy-1,4-pregnadiene-3,20-dione.

3. A compound as defined in claim 1 having the chemical name 16α-methyl-9,11-oxido-17α-dihydroxy-1,4-pregnadiene-3,20-dione 21-acetate.

* * * * *